US009987390B2

(12) United States Patent
Vogt

(10) Patent No.: US 9,987,390 B2
(45) Date of Patent: Jun. 5, 2018

(54) METHOD FOR PRODUCING AN ANTIBIOTIC POLYMETHYLMETHACRYLATE BONE CEMENT POWDER, AND AN ANTIBIOTIC POLYMETHYLMETHACRYLATE BONE CEMENT POWDER

(71) Applicant: Heraeus Medical GmbH, Wehrheim (DE)

(72) Inventor: Sebastian Vogt, Erfurt (DE)

(73) Assignee: HERAEUS MEDICAL, Wehrheim (DE)

( * ) Notice: Subject to any disclaimer, the term of this patent is extended or adjusted under 35 U.S.C. 154(b) by 87 days.

(21) Appl. No.: 14/855,757

(22) Filed: Sep. 16, 2015

(65) Prior Publication Data
US 2016/0082143 A1 Mar. 24, 2016

(30) Foreign Application Priority Data
Sep. 19, 2014 (DE) .......... 10 2014 218 913

(51) Int. Cl.
*A61L 24/00* (2006.01)
*A61L 27/16* (2006.01)
*A61L 24/06* (2006.01)
*A61L 27/54* (2006.01)

(52) U.S. Cl.
CPC .......... *A61L 24/0015* (2013.01); *A61L 24/06* (2013.01); *A61L 27/16* (2013.01); *A61L 27/54* (2013.01); *A61L 2300/406* (2013.01); *A61L 2430/02* (2013.01)

(58) Field of Classification Search
None
See application file for complete search history.

(56) References Cited

U.S. PATENT DOCUMENTS

| 5,162,309 | A | 11/1992 | Tentorio et al. | |
|---|---|---|---|---|
| 2006/0292199 | A1 | 12/2006 | Kuhn et al. | |
| 2008/0213336 | A1* | 9/2008 | Kuhn | A61L 24/0015 424/423 |
| 2008/0286377 | A1 | 11/2008 | Healey et al. | |
| 2010/0216697 | A1 | 8/2010 | Duewelhenke | |
| 2011/0054392 | A1* | 3/2011 | Nies | A61L 24/0036 604/82 |
| 2011/0257078 | A1* | 10/2011 | Young | A61K 31/336 514/2.7 |
| 2014/0072934 | A1 | 3/2014 | McKay | |
| 2016/0082143 | A1 | 3/2016 | Vogt | |

FOREIGN PATENT DOCUMENTS

| CA | 2434927 C | 2/2004 | |
|---|---|---|---|
| CN | 103223188 A | 7/2013 | |
| EP | 2018857 A1 | 1/2009 | |
| EP | 2997983 A1 | 3/2016 | |
| JP | 2006102512 A | 4/2006 | |
| JP | 2008183404 A | 8/2008 | |
| JP | 2010534213 A | 11/2010 | |
| WO | 2009013024 A1 | 1/2009 | |
| WO | WO 2009013024 A1 * | 1/2009 | ........... A61K 31/351 |
| WO | 2010029104 A2 | 3/2010 | |

OTHER PUBLICATIONS

European Pharmacopeia 5th ed. Main vol. 5.0, Strasbourg, Council of Europe, 2005, vol. 2, pp. 1638-1639.*
Australian Office Action for corresponding application AU 2015221496 dated Mar. 17, 2016.
Australian Office Action for corresponding application AU 2015221496 dated Oct. 24, 2016.
Canadian Office Action for corresponding application CA 2902354 dated Oct. 5, 2016.
Japanese Office Action and Translation for corresponding application JP 2015175419 dated Aug. 30, 2016.
European Pharmacopoeia, 5th Ed. Main vol. 5.0, Strasbourg: Council of Europe, France, 2004, vol. 2, ISBN 9287152810, p. 1638-1639.
S. S. Patel, et al. "Fosfomycin Tromethamine", Drugs, vol. 53, No. 4, pp. 637-656, 1997.
"Surgical Simplex P Radiopaque Bone Cement", published by Stryker Corporation, 2013, retrieved from the internet, http://www.stryker.co.jp, Japan, translation unavailable.

(Continued)

*Primary Examiner* — Carlos A Azpuru
*Assistant Examiner* — Casey S Hagopian
(74) *Attorney, Agent, or Firm* — Norris McLaughlin & Marcus PA

(57) ABSTRACT

The invention relates to a method for producing an antibiotic bone cement, whereby, in a step A), a bone cement base powder with a water content of less than or equal to 1.0% by weight is mixed with trometamol-fosfomycin to form a bone cement powder, and, in a step X), the bone cement powder is dried to a water content of less than or equal to 1.0% by weight. The invention also relates to a bone cement powder that was produced according to said method and contains a bone cement base powder and trometamol-fosfomycin, whereby the bone cement powder has a water content of less than or equal to 1.0% by weight. The bone cement powder is free-flowing and does not clump and can be used for producing bone cements that meet ISO 5833.

20 Claims, No Drawings

(56) References Cited

OTHER PUBLICATIONS

"Antibiotic (Fosfomycin) in bone cement", Clinical Orthopedics, 1987, vol. 22, No. 9, pp. 1073-1078, Japan, translation unavailable, Reference Article cited by Japanese Patent office in the Aug. 30, 2016 Office Action issued in corresponding application JP 2015175419.
German Search report for counterpart application DE 10 2014 218 913.6 dated Apr. 29, 2015.
J. Eitenmüller, et al., "Die Freisetzungsverzögerung verschiedener Antibiotica aus resorbierbarem Tricalciumphosphat-Keramikgranulat durch sie Verwendung löslicher Überzuge zur lokalen Behandlung der Osteomyelitis", Langenbecks Archiv für Chirurgie, 1983, vol. 360, pp. 193-206.
Chinese Office Action and Translation of Chinese Office Action for corresponding application CN 201510598445.9 dated Jan. 4, 2018.

\* cited by examiner

METHOD FOR PRODUCING AN ANTIBIOTIC POLYMETHYLMETHACRYLATE BONE CEMENT POWDER, AND AN ANTIBIOTIC POLYMETHYLMETHACRYLATE BONE CEMENT POWDER

This application claims foreign priority benefit under 35 U.S.C. § 119 of German Patent Application No. 10 2014 218 913.6, filed Sep. 19, 2014, the disclosures of which patent application is incorporated herein by reference.

The object of the invention includes a method for producing an antibiotic bone cement powder and the antibiotic bone cement powder produced by means of said method.

Articular endoprostheses are used extensively and very successfully in a broad range of articular diseases aiming to maintain the mobility of the patients. Unfortunately, a small fraction of the patients suffers infections at the articular endoprostheses and in the surrounding bone tissue and soft tissue. To treat these infections, it is very common to perform a one-stage or two-stage revision of the articular endoprosthesis.

Revision polymethylmethacrylate bone cements containing an antibiotic or two or more antibiotics have proven expedient for permanent mechanical fixation of the revision articular endoprostheses. Said antibiotics protect the revision articular endoprosthesis and the surrounding bone tissue and soft tissue, at least right after the surgery, from renewed microbial colonisation. Aside from individualised admixture of antibiotics by the physician, industrially produced revision polymethylmethacrylate bone cement have proven expedient.

Accordingly, Heraeus Medical GmbH manufactures and distributes the revision polymethylmethacrylate bone cements, Copal® G+C and Copal® G+V. Copal® G+C contains the combination of gentamicin and clindamycin. Copal® G+V contains the combination of gentamicin and vancomycin. The combination of gentamicin and vancomycin is particularly well-suited, thus far, if the infection of the articular endoprosthesis is caused by methicillin-resistant staphylococci (MRSA, MRSE).

However, vancomycin-resistant strains of staphylococci and enterococci have been known for a number of years as well. It is to be expected that these vancomycin-resistant bacteria will assume an increasing role as the causes of joint-associated infections in the near future. Therefore, it makes sense to develop a revision polymethylmethacrylate bone cement that contains at least one antibiotic possessing activity against vancomycin-resistant bacteria. Besides, increasingly problematic gram-negative bacteria also are significant as causes of joint-associated infections. This concerns, in particular, the so-called ESBL strains.

Fosfomycin is an antibiotic with a very broad range of activity. The antibiotic, fosfomycin ((2R,3S)-3-methyloxiranphosphonic acid, CAS 23155-02-4) was discovered in 1969 (D. Hendlin et al.: Phosphonomycin a new antibiotic produced by strains of *Streptomyces*. Science 96 (1969) 122-123.)

Fosfomycin inhibits the bacterial enzyme, MurA (UDP-N-acetylglucosamine-enolpyruvyl-transferase) (F. M. Kahan et al.: The mechanism of action of fosfomycin (phosphonomycin). Ann N Y Acad Sci 235 (1974) 364-386.; E. D. Brown et al.: "MurA (MurZ), the enzyme that catalyzes the first committed step in peptidoglycan biosynthesis, is essential in *Escherichia coli*. J. Bacteriol. 177 (14) (1995) 4194-4197). It catalyses the first step of murein biosynthesis. In this step, an enolpyruvil moiety based on phosphoenolpyruvate (PEP) is transferred to the hydroxyl group at position 3 of UDP-N-acetylglucosamine. This means that a lactic acid ether is generated at position 3 of UDP-N-acetylglucosamine. The disruption of this step by fosfomycin inhibits the bacterial cell wall synthesis.

Fosfomycin acts bactericidal in susceptible bacteria. Fosfomycin is active against both gram-negative and gram-positive bacteria including methicillin-resistant staphylococci (W. Graninger et al.: In vitro activity of fosfomycin against methicillin-susceptible and methicillin-resistant *Staphylococcus aureus*. Infection 12 (1984) 293-295). Fosfomycin is also efficacious against vancomycin-resistant *Staphylococcus aureus* (VRS) and vancomycin-resistant enterococci (F. Allerberger, I. Klare: In-vitro activity of fosfomycin against vancomycin-resistant enterococci. J Antimicrob Chemother 43 (1999) 211-217; T. Hara et al.: Antimicrobial activity of fosfomycin against beta-lactamase-producing methicillin-sensitive *Staphylococcus aureus* and methicillin-sensitive coagulase-negative staphylococci. Jpn J Antibiot 56 (20013) 142-147). In addition, fosfomycin is also efficacious against ESBL (M. E. Falagas et al.: Fosfomycin for the treatment of multidrug-resistant, including extended-spectrum R-lactamase producing enterobacteriaceae infections: a systematic review. Lancet Infect Dis 10 (2010) 43-50).

For pharmaceutical use, fosfomycin is converted to salts that are sufficiently stable during storage and form aqueous solutions that have a physiologically tolerable pH value. The European Pharmacopoeia describes three fosfomycin salts. These are the monohydrate of the calcium salt of fosfomycin (CAS 26016-98-8), the disodium salt of fosfomycin (CAS 26016-99-9), and trometamol-fosfomycin (CAS 78964-85-9).

The salts of fosfomycin are extraordinarily hygroscopic. They attract atmospheric humidity and deliquesce in the process. Experiments have shown that the salts, in the dry state, can be integrated into cement powders of polymethylmethacrylate bone cements. However, said cement powders also attract atmospheric humidity when stored on air, upon which the antibiotic particles also deliquesce. This can cause the bone cement powder to clump. For this reason, the fosfomycin salts are only poorly suitable for industrial production of antibiotic polymethylmethacrylate bone cement powders.

It is the object of the invention to overcome the aforementioned disadvantages of the prior art. Specifically, it is the object of the invention to develop a suitable method for the production of a flowable and free-flowing bone cement powder containing fosfomycin. The bone cement powder shall contain no clumps or other aggregates and shall be available as a flowable and free-flowing powder for medical applications.

The object of the invention was met by a method for producing an antibiotic bone cement, whereby, in a step A), a bone cement base powder with a water content of less than or equal to 1.0% by weight is mixed with trometamol-fosfomycin to form a bone cement powder, and the bone cement powder is dried to a water content of less than or equal to 1.0% by weight. The object of the invention is also met by a bone cement powder. The invention also relates to a bone cement powder that was produced according to a method of this type and contains a bone cement base powder and trometamol-fosfomycin, whereby the bone cement powder has a water content of less than or equal to 1.0% by weight.

In the scope of the invention, a bone cement base powder shall be understood to be organic or inorganic bone replacement raw materials in the form of a powder. Inorganic bone replacement raw materials include, for example, calcium phosphate or calcium sulfate, whereas organic bone replacement materials are polymers, in particular acrylate polymers. The polymer can be a homopolymer or a copolymer. Preferably the bone cement base powder is a polymer or copolymer of a methacrylic acid ester in the form of a powder. According to a particularly preferred embodiment, the polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), poly(styrene-co-methylmethacrylate), and a mixture of at least two of said polymers.

The amount of bone cement base powder that is admixed to the bone cement powder preferably ranges from 70 to 99.5% by weight, particularly preferably from 80.0 to 94% by weight.

The invention is based on the surprising observation that the method according to the invention can be used with the combination of trometamol-fosfomycin and generally known bone cement raw materials, in particular polymethylmethacrylate bone cement raw materials in the form of a powder, to produce a non-clumping bone cement powder that is suitable for storage.

Preferably, a polymerisation initiator is also admixed to the bone cement powder. The polymerisation initiator preferably is an activatable polymerisation initiator, e.g. peroxides and barbituric acid derivatives.

According to the invention, a peroxide is understood to mean compounds that contain at least one peroxo group (—O—O—). The peroxide preferably comprises no free acid groups. The peroxide can be an inorganic peroxide or an organic peroxide, such as, for example, dialkylperoxides or hydroperoxides. For example, the peroxide can be selected from the group consisting of dibenzoylperoxide, cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two of these substances. According to a preferred embodiment, the peroxide is selected from the group consisting of dibenzoyl peroxide and dilauroyl peroxide. Waterphlegmatised dibenzoylperoxide with a water content of less than 30% by weight is particularly preferred, 28% by weight is preferred.

The barbituric acid derivative is a barbituric acid derivative selected from the group consisting of 1-mono-substituted barbiturates, 5-mono-substituted barbiturates, 1,5-di-substituted barbiturates, and 1,3,5-tri-substituted barbiturates. The barbituric acid derivative selected from the group consisting of 1,5-di-substituted barbiturates and 1,3,5-tri-substituted barbiturates is preferred. There is no limitation with regard to the type of substituents on the barbituric acid. The substituents can, for example, be aliphatic or aromatic substituents. According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

A photo initiator or photo initiator system is also conceivable. In addition to the activatable polymerisation initiator, and electrically conductive radiopaquer can also be admixed. Particles made of cobalt, iron, NdFeB, SmCo, cobalt-chromium steel, zirconium, hafnium, titanium, titanium-aluminium-silicon alloys, and titanium-niobium alloys having a particle size of 0.5-500 μm are particularly well-suited in this context. It is feasible to induce eddy currents in said electrically conductive radiopaquer through alternating magnetic fields with a frequency in the range of 500 Hz to 50 kHz which cause the opaquer to heat up. Due to heat transmission, the initiator is heated as well and induced to thermally disintegrate.

Preferably, the amount of the polymerisation initiator that is admixed to the bone cement powder is in the range of 0.01 to 10% by weight, more preferably in the range of 0.2 to 8% by weight, and even more preferably in the range of 0.5 to 5% by weight, each relative to the total weight of the bone cement powder.

According to a preferred embodiment of the method according to the invention, at least one radiopaquer is admixed to the bone cement powder. The radiopaquer can be a common radiopaquer in this field, preferably in particulate form. Suitable radiopaquers can be soluble or insoluble in the monomer for radical polymerisation. The radiopaquer is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts, such as calcium carbonate calcium sulfate. In this context, zirconium dioxide, barium sulfate, calcium carbonate, and calcium sulfate are preferred. Said radiopaquers preferably have a mean particle diameter in the range of 10 nm to 500 μm. The concentration of admixed radiopaquer, in particular the zirconium dioxide concentration, in the bone cement powder is preferably in the range of 3 to 30% by weight, particularly preferably in the range of 5.0 to 20% by weight.

According to a further preferred embodiment of the invention, at least one further pharmaceutical agent can be admixed to the bone cement powder. The at least one further pharmaceutical agent can preferably be selected from the group consisting of antibiotics, antiphlogistic agents, steroids, hormones, growth factors, bisphosphonates, cytostatic agents, and gene vectors. According to a particularly preferred embodiment, the at least one pharmaceutical agent is an antibiotic. Preferably, the at least one antibiotic is selected from the group consisting of aminoglycoside antibiotics, glycopeptide antibiotics, lincosamide antibiotics, gyrase inhibitors, carbapenems, cyclic lipopeptides, glycylcyclines, oxazolidones, and polypeptide antibiotics, particularly preferably from the group of the aminoglycoside antibiotics, glycopeptide antibiotics, lincosamine antibiotics, lincosamide antibiotics, oxazolidinone antibiotics, and cyclic lipopeptides. According to a particularly preferred embodiment, the at least one antibiotic is a member selected from the group consisting of gentamicin, tobramycin, amikacin, vancomycin, teicoplanin, clindamycin, ramoplanin, metronidazole, and daptomycin, as well as salts and esters thereof. The at least one antiphlogistic agent is preferably selected from the group consisting of non-steroidal antiphlogistic agents and glucocorticoids. According to a particularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone. The at least one hormone is preferably selected from the group consisting of serotonin, somatotropin, testosterone, and estrogen. Preferably, the at least one growth factor is selected from the group consisting of fibroblast growth factor (FGF), transforming growth factor (TGF), platelet derived growth factor (PDGF), epidermal growth factor (EGF), vascular endothelial growth factor (VEGF), insulin-like growth factors (IGF), hepatocyte growth factor (HGF), bone morphogenetic protein (BMP), interleukin-1B, interleukin 8, and nerve growth factor. The at least one cytostatic agent is preferably selected from the group consisting of alkylating agents, platinum analogues, intercalating agents, mitosis inhibitors, taxanes, topoisomerase inhibitors, and antimetabolites. The at least one bisphosphonate is preferably selected from the group consisting of zoledronate and aledronate.

Preferably, the admixed amount of the further pharmaceutical agent or agents ranges from 0.1 to 15% by weight, preferably ranges from 0.3 to 12% by weight, relative to the total weight of the bone cement powder.

Following the mixing of the bone cement components, the bone cement powder is being sterilised. Methods for sterilisation of polymerisable monomers are known in the field of medical products.

It is essential to the method according to the invention that the water content of the raw materials used does not exceed the specified limits and that the bone cement powder is dried to a water content of less than or equal to 1.0% by weight.

According to the invention, it is advantageous to initially package the bone cement powder in a sterile packaging. In this context any packaging that meets the requirements for medical and pharmaceutical packaging and allows for sterilisation of the content is suitable. Pertinent examples include composite materials made of polyethylene film or polypropylene film and Tyvek®, a flash-spun fibre material made of high density polyethylene.

Aside from the common sterilisation methods, it is customary to use chemical compounds for sterilisation of medical products. Sterilisation with a mixture of ethylene oxide, water vapour, and carbon dioxide is proven to be particularly well-suited for the present method.

Subsequently, the bone cement powder is dried to a water content of less than or equal to 1.0% by weight. The drying of the bone cement powder can be performed according to known methods. The drying can be effected, for example, in a flow of hot air, preferably, in a vacuum.

After the drying, the bone cement powder that was sterilised inside the sterile packaging material is packaged in another packaging material that is impermeable for water vapour. Suitable packaging materials are metal vapour-tight packaging materials made of polypropylene or polyethylene of high density, such as, e.g., composite films having an aluminium layer or blister. Solid contains, e.g. made of aluminium, are also conceivable though. Aluminium composite film and aluminium-laminated paper are preferred as water vapour-impermeable packaging material.

Polymethylmethacrylate bone cements usually are present as two-component systems. The first component usually is a bone cement powder. The bone cement powder is also referred to as polymethylmethacrylate bone cement powder. The second component contains a polymerisable monomer, usually methylmethacrylate, and usually is a liquid. Mixing the two components results in a plastically deformable bone cement dough that hardens (cures) after a certain period of time.

The bone cement powder according to the invention can be used, by mixing with common monomer liquid that is composed, e.g., of methylmethacrylate, N,N-dimethyl-p-toluidine, p-hydroquinone, to produce a plastically deformable bone cement dough, which, after it is cured, meets the requirements of ISO 5833 with regard to the flexural strength being at least 50 MPa, the flexural modulus being at least 1,800 MPa, and the compressive strength being at least 70 MPa.

The polymethylmethacrylate cement powder according to the invention is particularly well-suited as a component of revision polymethylmethacrylate bone cements, for the production of spacers, and for the production of implantable local active substance release systems. Polymethylmethacrylate bone cements for revision purposes shall be understood to mean polymethylmethacrylate bone cements intended for permanent fixation of revision articular endoprostheses used in the scope of a one-stage or two-stage septic revision of infected articular endoprostheses. The term, spacer, shall be understood to mean temporary implants that are inserted, as temporary place-holders, in the scope of the two-stage septic revision of infected articular endoprostheses. The polymethylmethacrylate bone cement powder can just as well be used to produce local active substance release systems, whereby the bone cement powder is mixed with common mixtures of methylmethacrylate and a tertiary amine, e.g. N,N-dimethyl-p-toluidine, whereby a self-curing cement dough is produced that can be cast or modelled into any shape, whereby mechanically stable form bodies are produced after curing by means of radical polymerisation. These can be used in the scope of local antibiotics therapy. The active substance release systems can be provided to be spherical, bean-shaped, rod-shaped. It is feasible just as well to attach spherical or bean-shaped form bodies to biocompatible wires.

The invention shall be illustrated through the following examples, though without limiting the scope of the invention.

EXEMPLARY EMBODIMENTS

Inventive powders B1-4 each were produced by grinding the components in a three-dimensional shaker-mixer (Turbula® mixer, Willy A. Bachofen AG Maschinenfabrik, Muttenz, Switzerland).

For each of the inventive powders, a mixture of 88.53 g polymethylmethacrylate-co-methylacrylate (water content 0.78% by weight, determined by Karl-Fischer titration), 10.00 g zirconium dioxide, and 1.47 g dibenzoylperoxid (dibenzoylperoxid phlegmatised by 25% by weight water).

In addition, the amounts of trometamol-fosfomycin from Ecros (Spain) listed in Table 1 were added to inventive powders B1-4.

TABLE 1

| | Composition of the bone cement powder | | |
|---|---|---|---|
| Example | Bone cement powder with no active substance added | Trometamol-fosfomycin* | Gentamicin sulfate ** |
| B1 | 40.0 g | 1.88 g | — |
| B2 | 40.0 g | 2.82 g | — |
| B3 | 40.0 g | 3.76 g | — |
| B4 | 40.0 g | 2.82 g | 0.9 |

*Activity coefficient trometamol-fosfomycin 533
** Activity coefficient gentamicin sulfate 571

The bone cement powder of examples B1-4 was then sterilised with a mixture of ethylene oxide, water vapour, and carbon dioxide. Then, the bone cement powder was dried to a water content of less than 1.0% by the effect of a vacuum. After the drying, the bone cement powder of examples B1-4 was a free flowing, non-clumped powder.

The water content of the ethylene oxide-sterilized and subsequently dried bone cement powder of examples B1-4 was determined using the Karl-Fischer titration method. A Metrohm 802Tistand titrator was used for this purpose. The results are shown in Table 2.

TABLE 2

| Example | Water content wt. % |
|---|---|
| B1 | 0.53 |
| B2 | 0.51 |
| B3 | 0.52 |
| B4 | 0.87 |

Moreover, the sterilised and dried bone cement powders and Palacos® monomer liquid from Heraeus Medical GmbH, Wehrheim, Germany, composed of methylmethacrylate, hydroquinone, N,N-dimethyl-p-toluidine, and E141 colourant, were used to produce form bodies for the determination of the mechanical parameters in accordance with ISO 5833. The compositions of the bone cements are shown in Table 3.

TABLE 3

| | Composition of the cement dough | |
|---|---|---|
| Example | Bone cement powder | Monomer liquid |
| B1 | 41.9 g | 20 ml |
| B2 | 42.8 g | 20 ml |
| B3 | 43.8 g | 20 ml |
| B4 | 43.7 g | 20 ml |

The pastes B1-4 were used to produce strip-shaped test bodies with dimensions of (75 mm×10 mm×3.3 mm) for the determination of bending strength and flexural modulus and cylindrical test bodies (diameter 6 mm, height 12 mm) for the determination of the compressive strength. The test bodies were then stored for 24 hours on air at 23±1° C. Then the 4-point flexural strength, flexural modulus, and the compressive strength of the test bodies were determined using a Zwick universal testing device. The results are shown in Table 4.

TABLE 4

| Example | 4-point flexural strength [MPa] | Flexural modulus [MPa] | Compressive strength [MPa] |
|---|---|---|---|
| B1 | 70.5 ± 1.5 | 2949 ± 92 | 98.2 ± 2.4 |
| B2 | 73.1 ± 1.3 | 3211 ± 40 | 98.4 ± 1.6 |
| B3 | 65.2 ± 2.2 | 2923 ± 88 | 90.1 ± 0.9 |
| B4 | 64.7 ± 1.2 | 2903 ± 53 | 98.3 ± 1.7 |

The results of the 4-point flexural strength, flexural modulus, and compressive strength tests on the test bodies made from pastes B1-4 show that the mechanical stability requirements of ISO 5833 are met. ISO 5833 defines the following parameters: 4-point flexural strength of at least 50 MPa, flexural modulus of at least 1,800 MPa, and compressive strength of at least 70 MPa.

The invention claimed is:

1. A method for producing an antibiotic bone cement, comprising:
    step A), mixing a bone cement base powder with a water content of less than or equal to 1.0% by weight with trometamol-fosfomycin to form a bone cement powder, and
    step X), drying the bone cement powder to a water content of less than or equal to 1.0% by weight.

2. The method according to claim 1, wherein the bone cement base powder is a polymer powder comprising a polymer selected from the group consisting of poly(methacrylic acid methylester), poly(methacrylic acid ethylester), poly(methylmethacrylic acid propylester), poly(methacrylic acid isopropylester), poly(methyl-methacrylate-co-methylacrylate), poly(styrene-co-methylmethacrylate), and a mixture of at least two of said polymers.

3. The method according to claim 1, wherein, in step A), the amount of bone cement base powder that is admixed to the bone cement powder ranges from 70 to 99.5% by weight.

4. The method according to claim 1, wherein a radiopaquer is additionally admixed to the bone cement powder in step A).

5. The method according to claim 4, wherein the amount of admixed radiopaquer is in the range from 3 to 30% by weight.

6. The method according to claim 1, wherein an initiator is additionally admixed to the bone cement powder in step A).

7. The method according to claim 6, wherein the initiator is a peroxide.

8. The method according to claim 6, wherein the amount of admixed initiator is in the range of 0.01 to 10% by weight relative to the total weight of the bone cement powder.

9. The method according to claim 1, wherein a further pharmaceutical agent is additionally admixed in step A).

10. The method according to claim 9, wherein the pharmaceutical agent is an antibiotic that has a water content of maximally 15.0% by weight.

11. The method according to claim 9, wherein the admixed amount of the further pharmaceutical agent is in the range from 0.1 to 15% by weight, relative to the total weight of the bone cement powder.

12. The method according to claim 1, wherein the bone cement powder is sterilised in a step E) that proceeds after step A) and before step X).

13. The method according to claim 12, wherein the bone cement powder produced in step A) is packaged in a sterile packaging material in a step D) preceding step E).

14. A bone cement powder produced according to the method according to claim 1 which comprises a bone cement base powder and trometamol-fosfomycin, whereby the bone cement powder has a water content of less than or equal to 1.0% by weight.

15. The bone cement powder according to claim 14, comprising:
    75.0-90.0% by weight of at least one particulate polymethylmethacrylate or polymethylmethacrylate copolymer, relative to the total weight of the bone cement powder,
    5.0-20.0% by weight of a particulate radiopaquer, relative to the total weight of the bone cement powder,
    0.5-2.0 wt. % water-phlegmatised dibenzoylperoxide, relative to the total weight of the bone cement powder, having a water content of less than or equal to 30% by weight, and
    0.5-15.0 wt. % trometamol-fosfomycin, relative to the total weight of the bone cement powder, whereby the total water content of the bone cement powder is less than or equal to 1.0% by weight.

16. The bone cement powder according to claim 15, comprising an additional antibiotic selected from the group consisting of aminoglycoside antibiotics, glycopeptide antibiotics, lincosamide antibiotics, and oxazolidinone antibiotics, whereby the antibiotic has a water content of maximally 15.0% by weight.

17. A spacer or implantable local active substance release systems comprising a bone cement powder according to claim 14 as a component of polymethylmethacrylate bone cements.

18. The method according to claim 3, wherein, in step A), the amount of bone cement base powder that is admixed to the bone cement powder ranges from 80.0 to 94% by weight.

19. The method according to claim 5, wherein the amount of admixed radiopaquer is in the range from 5.0 to 20% by weight.

20. The method according to claim 7, wherein the initiator is a water phlegmatised dibenzoylperoxide with a water content of less than 28.0% by weight.

* * * * *